US00PP24690P3

(12) United States Plant Patent
Egger

(10) Patent No.: US PP24,690 P3
(45) Date of Patent: Jul. 22, 2014

(54) ***XHEUCHERELLA* PLANT NAMED 'CRACKED ICE'**

(50) Latin Name: *XHeucherella*
Varietal Denomination: Cracked Ice

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 206 days.

(21) Appl. No.: 13/507,937

(22) Filed: Aug. 7, 2012

(65) Prior Publication Data

US 2014/0047611 P1 Feb. 13, 2014

(51) Int. Cl.
*A01H 5/00* (2006.01)

(52) U.S. Cl.
USPC ..... Plt./441

(58) Field of Classification Search
CPC ..... A01H 5/02; A01H 5/00
USPC ..... Plt./441
See application file for complete search history.

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by medium size, palmatifid leaves with prominent sinuses, silver veiled leaves that change background colors from purple tinted green to copper tinted, prominent dark veins in summer through winter leaves, a low mounding plant habit, grows equally well in full sun or filtered shade in the Pacific Northwest, and excellent vigor.

1 Drawing Sheet

Botanical denomination: ×*Heucherella.*
Variety designation: 'Cracked Ice'.

BACKGROUND OF THE INVENTION

The present invention relates to a new and distinct cultivar of ×*Heucherella* and given the cultivar name of 'Cracked Ice'. ×*Heucherella* is in the family Saxifragaceae. ×*Heucherella* 'Cracked Ice' originated from a controlled cross between *Heuchera* K326-5 (a proprietary unreleased *Heuchera* hybrid), as the seed parent, and *Tiarella* 58-7 (a proprietary unreleased *Tiarella* hybrid), as the pollen parent.

Compared to the seed parent, *Heuchera* K326-5 (unpatented), the new cultivar has leaves that are more lobed and flowers that are white rather than purple pink.

Compared to the pollen parent, *Tiarella* 58-7 (unpatented), the new cultivar has silver rather than green leaves.

Compared to ×*Heucherella* 'Quicksilver' U.S. Plant Pat. No. 11,081, the new cultivar has leaves that are more deeply lobed and with more dark, prominent veins.

Compared to ×*Heucherella* 'Gunsmoke', U.S. Plant Pat. No. 22,395, the new cultivar has a smaller habit that is tighter and denser, shorter flowers, leaves that are more silver, glossier, and have round sinuses in terminal lobes on mature leaves.

This new ×*Heucherella* is distinguished by:

1. medium size, palmatifid leaves with prominent sinuses,
2. silver veiled leaves that change background colors from purple tinted green to copper tinted,
3. prominent dark veins in summer through winter leaves
4. a low mounding plant habit,
5. grows equally well in full sun or filtered shade in the Pacific Northwest, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old ×*Heucherella* 'Cracked Ice' growing in the ground in the garden in late fall in sun in Canby, Oreg.

FIG. 2 shows a one-year-old ×*Heucherella* 'Cracked Ice' in flower, planted in the ground in a trial bed in the sun in the summer in Canby, Oreg.

DETAILED PLANT DESCRIPTION

The following is a detailed description of the new ×*Heucherella* cultivar based on observations of two-year-old specimens growing in one gallon containers in a cold greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart*, fifth edition.

Plant:

*Form.*—Basal rosette, herbaceous perennial.
*Hardiness.*—USDA Zone 4 to 9.
*Size.*—14 cm tall from top of the foliage to the ground and 31 cm wide.
*Habit.*—Mounding.
*Vigor.*—Excellent.

*Roots.*—Fibrous, freely branching, fine, and white in color. Roots develop easily from cuttings.

Leaf:

*Type.*—Simple.

*Arrangement.*—Rosette.

*Shape.*—Ovate.

*Lobing/division.*—5 to 7 lobes palmately parted with the terminal the longest and most deeply parted usually with round sinuses that cup upwards; shallower secondary lobes.

*Venation.*—Palmate.

*Margins.*—Crenate.

*Apex.*—Mucronulate.

*Base.*—Cordate, lobes sometimes curl upwards.

*Blade size.*—Grows to 14.5 cm long and 9 cm wide.

*Surface texture.*—Glandular both surfaces.

*Petiole description.*—Grows to 13 cm long and 2 mm wide, glandular hairs, Greyed Orange 177A.

*Leaf color.*—Spring and fall, topside, between Black 202C and White NN155C with veins Greyed Purple N186B and margins Greyed Purple 197B (new leaves Greyed Orange 174A along veins and giving a red cast to the leaves through the veil of White NN155C), bottom side closest to Purple N77C; summer, winter, topside closest to Black 202C with veins and edges Greyed Purple N186A (younger leaves have a purple cast from the Greyed Purple N186A), bottom side closest to Purple N77C; older shaded leaves Green N137B with veil of Greyed Green 190B and main veins Greyed Purple 187A.

Inflorescence:

*Size.*—Grows to 3.5 cm wide and 26 cm long.

*Type.*—Raceme.

*Number of flowers per raceme.*—About 70.

*Number of raceme.*—7 in first spring flush, repeat blooms.

*Peduncle.*—Grows to 17 cm tall, 4 mm wide at base, Greyed Brown N199B, glandular hairs.

*Pedicel.*—Variable, with glandular hairs, Greyed Purple 187A.

*Bloom period.*—May with sporadic rebloom in Canby, Oreg.

Flower bud:

*Size.*—2.5 mm wide and 4 mm long.

*Description.*—Glandular puberulent, ovoid.

*Color.*—Yellow Green 150D with tip Yellow Green 151A.

Flower:

*Type.*—Perfect.

*Shape.*—Campanulate.

*Size.*—4 mm deep and 7 mm wide.

*Petal description.*—5 in number, lanceolate, 4 mm long and 1 mm wide, tip acuminate, base attenuate, margin entire, glabrous on both sides, White NN155D on both sides.

*Calyx description.*—4 mm deep and 5 mm wide, with 5 lobes, divided ¾ way to the base, campanulate, glandular hairs on both sides, tip obtuse, margin entire, both sides NN155D with Yellow Green 151A on lobe tips.

*Stamen description.*—10 in number, filaments 3 mm long, White NN155D, anthers sterile, less than 1 mm, Greyed Orange N167A.

*Pistil description.*—One central two beaked pistil, 4 mm long and 2 mm wide, White NN155D.

*Fragrance.*—None.

*Lastingness.*—Each raceme blooms for about 2 weeks on the plant.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

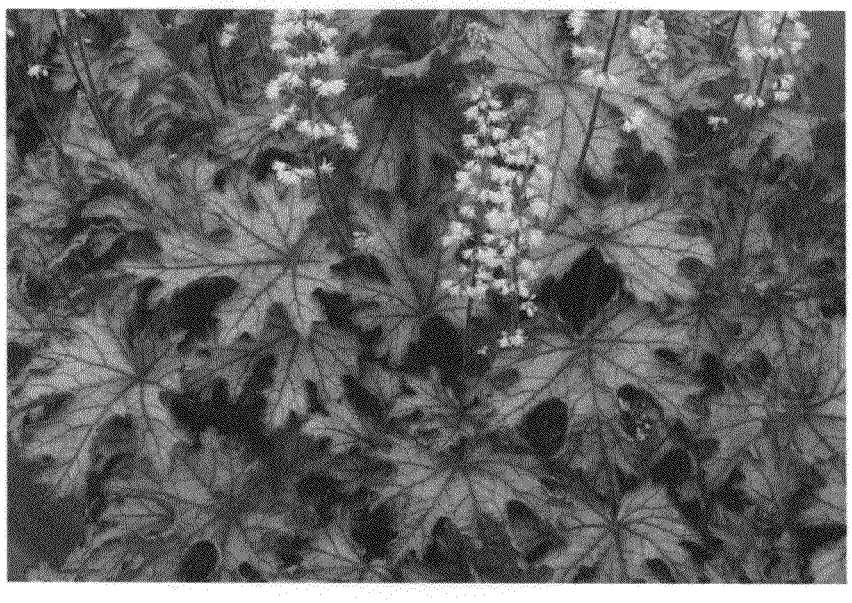

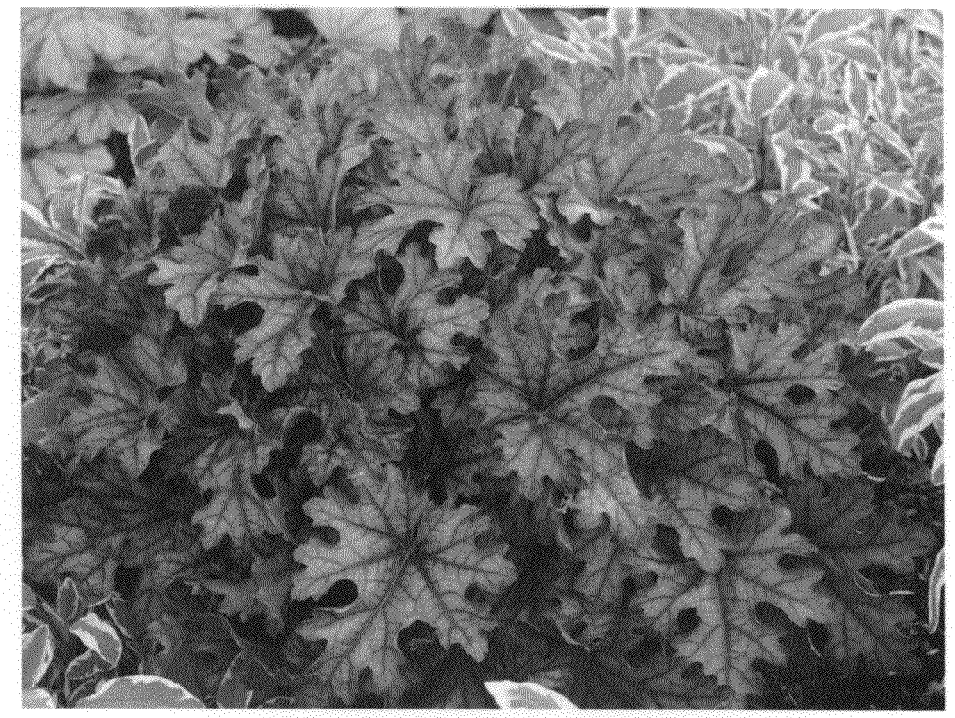
FIG. 1 above, FIG. 2 below